United States Patent
Volgas et al.

(10) Patent No.: US 8,426,341 B2
(45) Date of Patent: Apr. 23, 2013

(54) HERBICIDE FORMULATION

(75) Inventors: Greg Volgas, Bartlett, TN (US); Johnnie R. Roberts, Arlington, TN (US); Marvin Baker, III, Horn Lake, MS (US); Peter Delashmit, Memphis, TN (US)

(73) Assignee: Helena Holding CompanyDE (US)

( * ) Notice: Subject to any disclaimer, the term of this patent is extended or adjusted under 35 U.S.C. 154(b) by 2128 days.

(21) Appl. No.: 11/139,117

(22) Filed: May 27, 2005

(65) Prior Publication Data

US 2006/0270557 A1    Nov. 30, 2006

(51) Int. Cl.
*A01N 25/00*    (2006.01)

(52) U.S. Cl.
USPC .................................................. 504/116.1

(58) Field of Classification Search ............... 504/116.1
See application file for complete search history.

(56) References Cited

U.S. PATENT DOCUMENTS

| | | | |
|---|---|---|---|
| 3,682,849 A * | 8/1972 | Smith .................... | 568/622 |
| 3,755,339 A | 8/1973 | McKendry | |
| 3,761,486 A | 9/1973 | McGregor | |
| 3,894,149 A * | 7/1975 | Mast ...................... | 514/86 |
| 3,937,826 A | 2/1976 | Harris | |
| 4,445,925 A | 5/1984 | Young | |
| 4,470,840 A | 9/1984 | Welebir | |
| 4,767,448 A | 8/1988 | Nielsen | |
| 4,816,060 A | 3/1989 | Steller et al. | |
| 4,863,506 A | 9/1989 | Young | |
| 4,971,630 A | 11/1990 | Skaptason | |
| 4,994,101 A | 2/1991 | Young | |
| 4,995,900 A | 2/1991 | Futcher | |
| 5,096,711 A | 3/1992 | Dookhith et al. | |
| 5,118,338 A | 6/1992 | Moller | |
| 5,176,736 A | 1/1993 | Narayanan et al. | |
| 5,178,795 A | 1/1993 | Roberts | |
| 5,183,492 A | 2/1993 | Suchy et al. | |
| 5,189,414 A | 2/1993 | Tawara | |
| 5,206,021 A | 4/1993 | Dookhith et al. | |
| 5,221,319 A | 6/1993 | Van Haften et al. | |
| 5,234,919 A | 8/1993 | Roberts | |
| 5,254,344 A | 10/1993 | Dookhith et al. | |
| 5,268,352 A | 12/1993 | Dexter | |
| 5,270,286 A | 12/1993 | Ong | |
| 5,280,008 A | 1/1994 | Cahoy et al. | |
| 5,288,692 A | 2/1994 | Young | |
| 5,300,680 A | 4/1994 | Jones et al. | |
| 5,317,042 A | 5/1994 | Narayanan | |
| 5,328,889 A | 7/1994 | Van Haften et al. | |
| 5,393,791 A | 2/1995 | Roberts | |
| 5,416,067 A | 5/1995 | Van Haften et al. | |
| 5,510,322 A | 4/1996 | Young | |
| 5,529,975 A * | 6/1996 | Chamberlain ................ | 504/361 |
| 5,561,099 A | 10/1996 | Murphy et al. | |
| 5,565,409 A | 10/1996 | Sato et al. | |
| 5,580,567 A | 12/1996 | Roberts | |
| 5,668,085 A | 9/1997 | Forbes et al. | |
| 5,670,454 A | 9/1997 | Grossmann et al. | |
| 5,707,928 A | 1/1998 | Baker | |
| 5,725,630 A | 3/1998 | Roberts et al. | |
| 5,741,502 A | 4/1998 | Roberts | |
| 5,795,847 A | 8/1998 | Nielsen et al. | |
| 5,877,112 A | 3/1999 | Roberts et al. | |
| 5,906,961 A | 5/1999 | Roberts et al. | |
| 5,994,271 A | 11/1999 | Ravetta et al. | |
| 6,069,115 A | 5/2000 | Pallett et al. | |
| 6,071,857 A | 6/2000 | Vogt et al. | |
| 6,121,200 A | 9/2000 | Berger et al. | |
| 6,165,939 A | 12/2000 | Agbaje et al. | |
| 6,180,563 B1 | 1/2001 | Ruegg et al. | |
| 6,180,566 B1 | 1/2001 | Nielsen et al. | |
| 6,187,715 B1 | 2/2001 | Narayanan et al. | |
| 6,207,617 B1 | 3/2001 | Gillespie | |
| 6,232,272 B1 | 5/2001 | Roberts et al. | |
| 6,235,300 B1 | 5/2001 | Brumbaugh | |
| 6,355,799 B1 | 3/2002 | Gupta et al. | |
| 6,369,001 B1 | 4/2002 | Jimoh | |
| 6,589,913 B1 | 7/2003 | Killick et al. | |
| 6,803,345 B2 | 10/2004 | Herold et al. | |
| 2002/0107149 A1 | 8/2002 | Volgas et al. | |
| 2003/0144147 A1 | 7/2003 | Herold et al. | |
| 2003/0148889 A1 | 8/2003 | Herold et al. | |
| 2004/0167032 A1 | 8/2004 | Volgas et al. | |
| 2005/0288188 A1 | 12/2005 | Volgas et al. | |
| 2006/0270557 A1 | 11/2006 | Volgas et al. | |

FOREIGN PATENT DOCUMENTS

| | | |
|---|---|---|
| CA | 1225533 | 8/1987 |
| EP | 0 100 440 | 2/1984 |
| EP | 0 163 598 | 12/1985 |
| EP | 0 216 126 | 4/1987 |

(Continued)

OTHER PUBLICATIONS

URL<http://www.se.akzonobel.com/cleaning/brochures/Berol_260_266_and_840_Narrow_range_ethoxylates.pdf>, 2003, Berol 260, 266 and 840:Narrow Range ethoxylated alcohols.*
Weedone® 638 from Rhone-Poulenc Nov. 13, 1998.
Albaugh® D-638 from Aulbaugh, Inc. Oct. 2, 1998.
Milton J. Rosen, "Surfactants and Interfacial Phenomena," John Wiley & Sons, pp. 239-240 (1978).
Briggs et al., "Physico-chemical Factors Affecting Uptake by Roots and Translocation to Shoots of Weak Acids in Barley, " Pesticide Science, vol. 19, pp. 101-112 (1987).
Wyrill, J.B. et al., "Glyphosate Toxicity to Common Milkweed and Hemp Dogbane as Influenced by Surfactants," Weed Science, vol. 25, No. 3 pp. 275-287 (May 1977).
Tomlin, C., Ed., The Pesticide Manual, Tenth Edition, p. 1338, (1995).

(Continued)

*Primary Examiner* — Rebecca Prouty
*Assistant Examiner* — Danielle Sullivan
(74) *Attorney, Agent, or Firm* — Novak Druce Connolly Bove + Quigg LLP

(57) ABSTRACT

A composition containing a herbicide compound in acid form and an alcohol ethoxylate surfactant, wherein the composition contains less than 2.0% free un-reacted alcohol.

30 Claims, No Drawings

FOREIGN PATENT DOCUMENTS

| | | |
|---|---|---|
| EP | 0 217 125 | 4/1987 |
| EP | 0 243 522 | 11/1987 |
| EP | 0 334 041 | 9/1989 |
| EP | 0 357 553 | 3/1990 |
| EP | 0 371 212 | 6/1990 |
| EP | 0371212 | 6/1990 |
| EP | 0 433 577 | 6/1991 |
| EP | 0 454 968 | 11/1991 |
| EP | 0 554 015 | 8/1993 |
| EP | 0 641 161 | 3/1995 |
| EP | 0 703 724 | 4/1996 |
| GB | 2 230 955 | 11/1990 |
| GB | 2 267 825 | 12/1993 |
| JP | 58-85805 | 5/1983 |
| RU | 2 073 974 | 2/1997 |
| RU | 19930007423 | 2/1997 |
| WO | WO-92/21686 | 12/1992 |
| WO | WO-94/00986 | 1/1994 |
| WO | WO-94/19941 | 9/1994 |
| WO | WO-96/08150 | 3/1996 |
| WO | WO-97/37978 | 10/1997 |
| WO | WO-98/17109 | 4/1998 |
| WO | WO-99/55155 | 11/1999 |
| WO | WO-00/42847 | 7/2000 |
| WO | WO-00/67571 | 11/2000 |
| WO | WO-01/52650 | 7/2001 |
| WO | WO-02/11536 | 2/2002 |

* cited by examiner

HERBICIDE FORMULATION

BACKGROUND OF THE INVENTION

Commercially available herbicide compositions include a very large variety of active herbicide compounds. Herbicide compositions can be prepared from a variety of different types of precursor compositions, and can be commercially available and used in a variety of different types of compositions, including compositions referred to as wettable powders, water dispersible granules, granules, aqueous solutions, water soluble powders, emulsifiable concentrates, oil-based flowables, concentrated emulsions, suspo-emulsions, emulsions, suspensions, suspension concentrates, mixtures, dispersions, and microemulsions, as well as others. Any of these different types of compositions may have different advantages or disadvantages depending on what type of active ingredients the herbicide includes.

Many of these compositions contain water-soluble salts of chlorinated carboxylic acid herbicides. These salts, often alkylamine salts or metal salts, are generally not as active as their acid equivalents. For example, (2,4-dichlorophenoxy) acetic acid ("2,4-D") acid is known to be more herbicidally active than the dimethylamine salt of 2,4-D. Also, many of the chlorinated carboxylic acid herbicides are sold to the end users as esters because these esters are more active than the corresponding amine formulation. For instance, it is generally known that 2,4-D ester formulations are more effective as herbicides than 2,4-D amine formulations. The esters, however, are more likely to volatilize even after deposition onto target areas. After volatilization, these esters can cause significant damage to off-target plants.

Acid herbicides are usually have traditionally been reacted into amine or other salts, which are soluble in water, or into esters which are oil soluble. Both salts and esters must then break down in the environment back into the acid, which is herbicidal.

It would be preferable, then, to apply the herbicides as acids. However, they are not significantly soluble in water. Previously, solvents used to formulate 2,4-D acid such as xylene range hydrocarbons, are known to be phytotoxic to plants and may enhance herbicide volatility and subsequent drift to non-target areas. Albaugh D-638 is one such product, but it further incorporates the ester form of 2,4-D into the formulation. The formulation is 24.5% by weight of 2-butoxyethyl ester of 2,4-dichlorophenoxyacetic acid (CAS #1929-73-3), 13.8% by weight 2,4-D (CAS #94-75-7) and a solvent that contains 7.7% by weight naphthalene (CAS #91-20-3). It is believed that the solvent is Aromatic 150. It is believed that solvent is present in an amount from 55 to 60%. Another commercial product containing the acid form of 2,4-dichlorophenoxyacetic acid is WEEDONE® 638 from Rhone Poulenc (now marketed by Nufarm). This formulation contains 25.2% of the 2-ethylhexyl ester of 2,4-D, 13.8% of the acid form of 2,4-D, 3% propylene glycol, 1.5% titanium oxide and other undisclosed inerts. This formulation is believed to be described in one of the following patents: U.S. Pat. Nos. 5,254,344, 5,096,711, or 5,206,021. The 2,4-D in this formulation is not solubolized, but has been dispersed through a water phase.

Another problem associated with the amine salts of some chlorinated carboxylic acid herbicides is their inability to mix with fertilizers. 2,4-D amine herbicides cannot be mixed directly into Uran (urea-ammonia nitrate) fertilizer without some dilution in water. This is a disadvantage for applicators, since this dilution practice increase the total spray volume they must apply per acre.

Surfactants are used in most agricultural formulations to enhance the ease of application. Since many pesticide formulations use hydrophobic solvents, requiring the use of surfactants to emulsify the hydrophobic solvent and pesticide into water. Surfactants have also been used both as adjuvants and formulation components to enhance the effectiveness and spreading ability of applied sprays.

Examples of just a few available active herbicide compounds include those herbicides from the class of the hydroxylamines, for example sethoxidim, alloxydim, clethodim, cycloxydim, tepralkoxydim, tralkoxydim or butroxidim;

herbicides from the class of the imidazolinones, such as imazethapyr, imazamethabenz, imazamethapyr, imazaquin, imazamox or imazapyr;

herbicides from the class of the pyrimidines, such as pyrithiobac-sodium, pyriminobac, bispyribac-sodium;

herbicides from the class of the PPO, for example nitrofen, bifenox, acifluorfen, lactofen, oxyfluorfen, ethoxyfen, fluoroglycofen, fomesafen, halosafen, azafenidin (CAS RN.-68049-83-2), benzfendizone (CAS RN 158755-954), butafenacil (known from U.S. Pat. No. 5,183,492, CAS RN 158755-95-4), carfentrazone-ethyl, cinidon-ethyl (CAS RN 142891-20-1), flumichlorac-pentyl, flumioxazin, fluthiacet-methyl, oxadiargyl, oxadiazon, pentoxazone, sulfentrazone, fluazolate (CAS RN 174514-07-9) or pyraflufen-ethyl;

herbicides from the class of the phenoxy acids, for example 2,4-D, Monochloro phenyoxy acidic acid (MCPA), Monochloro phenyoxy propionic acid (MCPP), MCPB, trichlorpyr or mecropop-P;

herbicides from the class of the benzoic acids, for example dicamba or picloram; herbicides from the class of the sulfonamides, for example flucarbazone (CAS RN 181274-17-9), procarbazone (CAS RN 145026-81-9), chlorasulam, diclosulam (CAS RN 145701-21-9), florasulam, flumetsulam or metosulam;

Herbicides from the class known as pyridine herbicides, (e.g., triclopyr, fluoroxypyr);

Herbicides from the class of benzoic acid herbicides, (e.g., dicamba acid);

herbicides from the class of aryloxy phenoxy propionic acid herbicides, (e.g., fluazifop acid and quizolofop acid); and water-insoluble diphenyl ether type herbicides (e.g., oxyfluorfen or acifluorfen).

Active herbicide ingredients such as these and others can be prepared from and used in the form of solid and liquid compositions including, as mentioned above, different forms of emulsions, suspensions, suspension concentrates, mixtures, dispersions, and microemulsions, etc. With regard to the liquid forms, the active ingredient (herbicide compound) is generally suspended or dissolved in a liquid, with the active herbicide compound taking the chemical form of a salt or ester, depending on which form is either soluble or suspendable in such a liquid composition. Most herbicide compositions are prepared from an ester or salt form of a herbicide compound, or are prepared using a step to convert an acid form of a herbicide compound to a salt or an ester to be either miscible in water or emulsifiable in water for application, often with the assistance of organic solvent.

With microemulsion compositions, in particular, earlier microemulsion work typically included the use of herbicide compounds in forms other than their acid forms, e.g., ester or salt forms, because the salt or ester forms were considered to be most easily dispersed or suspended in a microemulsion. Typical microemulsions also incorporated organic solvents to effect suspension or dissolution of the herbicide compound.

New forms of effective herbicide compositions are always desirable, especially those that show advantages in processing, application, environmental profile (e.g., volatility), or efficacy. And there is always a desire to prepare herbicide compositions that reduce or eliminate organic solvents.

U.S. patent application Ser. No. 09/916,611 describes an invention wherein the chlorinated carboxylic acid herbicide is dissolved in a surfactant. The examples provided in this application demonstrate the use of alcohol ethoxylates in most of the examples. In examples 2 through 5, other surfactants are used in place of the alcohol ethoxylates. The specific alcohol ethoxylates used were $C_{11}$ alcohol with 3 moles of EO and $C_{11}$ alcohol with 9 moles of EO. These alternate surfactants are nonylphenol 6 mole ethoxylate, a block copolymer (Pluronic), a sorbitan based surfactant, butyl cellusolve, and a phosphate ester of a $C_{11}$ alcohol with 6 moles of EO.

U.S. Pat. No. 6,803,345 (Herold, Beardmore and Parrish), describes herbicide compositions that are prepared from micro-emulsions containing herbicide compound in acid form, and methods of their preparation and use. There are other patents and applications in the U.S. and internationally that are related to this patent. These formulations also contain acid herbicides which are dissolved in surfactants. There are a number of examples shown in this patent. Nearly all of the examples provided include as major constituents, alcohol ethoxylates. Specifically, Tomadol 1-5, Tomadol 1-7, Surfonic L12-6 are used as major constituents of the first 17 examples. The next set of 5 examples use alternate surfactants. Specifically, in place of the alcohol ethoxylates of the first 17 examples, the surfactants are octyl- or nonyl-phenol ethoxylates, a castor oil ethoxylate, sorbitan based surfactants, or ethoxylated tristerylphenol.

In both patents, in all examples where alcohol ethoxylates were used, the specific alcohol ethoxylates contain high levels of free alcohol.

monly mixed with some surfactants, such as phosphate ester surfactants, can react with acid herbicides.

Previously, it was expected that the compositions would require temperature extremes as high as 200 degrees F. in order to make the alcohol and acid herbicide react. It has been found that this reaction occurs, albeit more slowly, at elevated temperatures much lower than 200 degrees F., and even at ambient temperatures. The reaction product of this free alcohol and acid herbicide is generally an ester of the acid herbicide. Ester forms of acid herbicides are generally much more volatile than their acid or amine forms.

It is possible to formulate acid herbicide compositions with little or no free alcohol. In this manner, the alcohol-acid herbicide reaction and decomposition is prevented.

One way of identifying a herbicide compound in acid form is to reference a pKa of a herbicide compound. The pKa of a herbicide compound is understood to refer to the negative logarithm (base 10) of the equilibrium constant K for the reaction of the herbicide compound between its acid form and its neutral form. Methods of determining the pKa for a herbicide compound will be readily understood by the skilled artisan. Exemplary herbicide compounds that are capable of existing in acid form can have a pKa below about 6, or below about 5 or 4. Some herbicide compounds include more than one acidic hydrogen and therefore have more than a single pKa value. According to the invention, the relevant and referred to pKa is the pKa of a herbicide compound that relates to the change of the compound between the compound considered to be the deprotonated "acid" form of the compound, and what is considered to be the protonated (neutral) form of the "acid" form. The protonated acid form predominates at pH below the pKa, and the deprotonated form predominates at pH above the pKa. Examples of exemplary pKa values for certain herbicide compounds are included in the Table 1.

| Surfactant used in examples shown in prior application and patent | % Free alcohol | Reference |
|---|---|---|
| $C_{11}$-3 EO | 16% | Tomah Products, Inc. Brochure entitled: *Tomadol Alcohol Ethoxylate Product Guide*, no date given. |
| $C_{11}$-9 EO | 2% | Tomah Products, Inc. Brochure entitled: *Tomadol Alcohol Ethoxylate Product Guide*, no date given |
| Tomadol 1-5 ($C_{11}$-5EO) | 5% | Tomah Products, Inc. Brochure entitled: *Tomadol Alcohol Ethoxylate Product Guide*, no date given |
| Tomadol 1-7 ($C_{11}$-EO) | 3% | Tomah Products, Inc. Brochure entitled: *Tomadol Alcohol Ethoxylate Product Guide*, no date given |
| Surfonic L12-6 ($C_{10-12}$-6EO) | Estimated at 5-7% | No data available from Hunstman. Data extrapolated from Tomah similar product in above reference. |
| Surfonic DDA-6 (Dodecyl alcohol (branched)-6EO) | Estimated at 5-7% | No data available from Hunstman. Data extrapolated from Tomah similar product in above reference. |
| Surfonic TDA-6 (Tridecyl alcohol (branched)-6EO) | Estimated at 5-7% | No data available from Hunstman. Data extrapolated from Tomah similar product in above reference. |

From the number of examples shown in the previous literature, it is clear that the $C_{11}$ alcohol ethoxylate was the most favorable surfactant.

It has been surprisingly discovered that the free alcohol in alcohol ethoxylates is capable of reacting with the acid herbicides of the prior inventions. Also, the free alcohol com- Some examples of useful herbicide compounds that can be used in their acid forms to produce microemulsion-forming-concentrates (MFC) in surfactant include the following, some or all of which are commercially available in their acid form (though presently not generally sold in that form as herbicide formulations). For herbicide compounds that are sold in a form other than the acid form, such as a salt or ester form, a skilled chemist will understand how to convert the non-acid to an acid form for use as described herein. For example, depending, e.g., on the herbicide compound and other factors, from about 0.05 to about 7 parts by volume MFC may be diluted with about 93 to about 99.95 parts by volume water to form a microemulsion. Other ingredients such as acidifying agent or other herbicides may also be added.

The class of phenoxy herbicides generally includes herbicides derived from chlorinated phenols, and includes herbicide compounds that can exist in an acid form. Examples include the well known herbicides 2,4-dichlorophenoxyacetic acid (known as 2,4-D), 4-methyl-4-chlorophenoxyacetic acid (MCPA Acid), and 2(-2-methyl-4-chlorophenoxy)propionic acid (MCPP acid), as well as others.

Pyridine herbicides are herbicides derived from a pyridine ring-containing compound, and includes herbicide compounds that can exist in an acid form. Examples include 3,5,6-trichloro-2-pyridyloxyacetic acid (triclopyr acid) and fluroxypyr (4-amino-3,5-dichloro-6-fluoro-2-pyridyloxyacetic acid), as well as others.

Benzoic acid herbicide compounds include or are derived from benzoic acid compounds. This class of herbicide compounds includes herbicide compounds that can exist in an acid form. A single example is dicamba acid (3,6-dichloro-O-anisic acid), but others could also be used according to the invention.

Aryloxy phenoxy propionic acid herbicide compounds (also referred to sometimes as "oxyphenoxy" herbicides), are another class of herbicides that can exist in an acid form. Examples of specific compounds include fluazifop acid and quizolofop acid, as well as others.

TABLE 1

| Acidic Herbicides: | pKas |
|---|---|
| Bromoxynil | 4.06 |
| Ioxynil | 3.96 |
| Bentazon | 3.30 |
| Dicamba | 1.87 |
| Diclofop | 3.57 |
| Fenoxaprop | NA |
| Fluazifop-p | 2.98 |
| Fosamine | NA |
| Glufosinate | 2, 2.9 |
| Glyphosate | 2.6, 5.6 |
| Haloxyfop | 2.9 |
| Imazamethbenz | 2.9 |
| Imazapyr | 1.9, 3.6 |
| Imazaquin | 3.8 |
| Imazamox | NA |
| Imazethapyr | 2.1, 3.9 |
| Picloram | 2.3 |
| Triclopyr | 2.68, 3.97 |
| Clopyralid | 2.3 |
| Floroxypyr | 2.94 |
| Quinclorac | 4.34 |
| Quizalofop-p | 1.25 |
| Sethoxydim | 4.16 |
| 2,4-D | 2.64 |
| 2,4-DB | 4.8 |
| Dichlorprop | 3.0 |
| MCPA | 3.07 |
| Mecoprop | 3.77 |
| Clethodim | |
| Acifluorfen | 3.86 |
| Dacthal | NA |
| Endothal | 3.4, 6.7 |
| Asulam | 4.82 |

(Where a pKa is listed as NA, a person of ordinary skill in the art would be able to identify the pKa.)

The herbicide compound in acid form is dissolved in surfactant (and optionally water and organic acid) to form a concentrate that contains surfactant and dissolved herbicide compound in acid form.

Provided that they do not contain free alcohol, additional surfactants can be added to this composition. A very large variety of surfactants are known and commercially available, including such different classes as cationic surfactants, anionic surfactants, non-ionic surfactants, ionic surfactants, and amphoteric surfactants. According to the invention, the surfactant can be any surfactant or combination of two or more surfactants useful to dissolve the herbicide compound in its acid form to produce a microemulsion-forming-concentrate.

Examples of some preferred additional surfactants that can be added to this composition include cationic, non-ionic, and anionic surfactants. Of these, some even more specific types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants. Examples of surfactants and identification of their intermediate and general classifications are as follows:

Alcohol alkoxylates including but not limited to:
Based on branched and linear alcohols
Those containing ethylene oxide or propylene oxide
Alcohol alkoxylate sulfates,
Alkylphenol alkoxylates including but not limited to:
Nonylphenol and octylphenols.
Those containing ethylene oxide or propylene oxide
Alkanolamides,
Alkylaryl sulfonates,
Amine oxides
Amines including but not limited to:
Fatty amine alkoxylates such as but not limited to tallowamine alkoxylates,
Betaine derivatives,
Block polymers of ethylene and propylene glycol,
Carboxylated alcohol or alkylphenol alkoxylates,
Diols, including but not limited to Butanediols,
Diphenyl sulfonate derivatives,
Ethers, including but not limited to
Butyl celluslose,
Butyl carbitol,
Ethoxylated amines,
Ethoxylated fatty acids,
Ethoxylated fatty esters and oils,
Ethoxylated triglycerides,
Fatty esters,
Glycerol esters,
Phosphate ester surfactants including but not limited to
Phosphate esters of alcohol alkoxylates,
Phosphate esters of alkylphenol alkoxylates,
Sarcosine derivatives,
Silicone-based surfactants,
Sorbitan derivatives including but not limited to:
Sorbitan esters,
Alkoxylated sorbitan esters,
Sucrose and glucose derivatives including but not limited to:
Alkylpolyglucosides,
Sulfates and sulfonates of alkoxylated alkylphenols,
Sulfates of alcohols,
Tristyrylphenol Alkoxylates, Other surfactants are disclosed in McCutcheon's Emulsifiers and Detergents, North American Edition, 2000.

The following examples were prepared:

COMPARATIVE EXAMPLE 1

The following composition was prepared without adding heat or a stirrer. All liquid components were added to the beaker first, then the herbicide, 2,4-D acid technical was added. Agitation was continued until the technical fully dissolved (c.a. 1 hour).

| | |
|---|---|
| 2,4-D acid technical (98%) | 20.0% |
| C11 alcohol ethoxylate | 47.75% |
| With 3 moles of EO | |
| (Contains 16% free alcohol) | |
| Tallowamine ethoxylate | 16.85% |
| Phosphate ester of an alcohol Ethoxylate | 13.40% |
| Water | 2.00% |

EXAMPLE 2

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| 2,4-D acid technical (98%) | 20.0% |
| C9-11 alcohol ethoxylate | 41.0% |
| With 3 moles of EO | |
| (Contains 1% free alcohol) | |
| Tallowamine ethoxylate | 16.85% |
| Phosphate ester of an alcohol Ethoxylate | 5.00% |
| Water | 17.15% |

Examples 1 and 2 were stored for 2 weeks at elevated temperatures (45 degrees C.). They were then analyzed using the A.O.A.C. method of analysis for 2,4-D with a minor change (the method calls for saponification of the active ingredient. However, esters of 2,4-D (should they form) would be saponified using the traditional method. Running the method without the saponification step allows analysis of the pure acid form of 2,4-D.

Analyses after 2 weeks

Example 1 57.6% of the initial 2,4-D remaining

Example 2 91.3% of the initial 2,4-D remaining

Examples 1 and 2 were both storage stable at ambient, 4 degrees C., and 45 degrees C. Both compositions mixed readily with Urea-ammonia nitrate fertilizer. Both compositions formed micro-emulsions in water.

EXAMPLE 3

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| 2,4-DB acid technical (99%) | 19.7% |
| C9-11 alcohol ethoxylate | 40.2% |
| With 3 moles of EO | |
| (Contains 1% free alcohol) | |
| Tallowamine ethoxylate | 30.1% |
| Water | 10.0% |

Example 3 was storage stable at ambient, 4 degrees C, and 45 degrees C. The composition mixed readily with Urea-ammonia nitrate fertilizer and formed a micro-emulsion in water.

EXAMPLE 4

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| Dicamba acid technical (98%) | 40.0% |
| C13 alcohol ethoxylate | 36.0% |
| With 6 moles of EO | |
| (Contains <1% free alcohol) | |
| Methylated fatty acids | 24.0% |

Example 4 was storage stable at ambient, 4 degrees C., and 45 degrees C. The composition mixed readily with Urea-ammonia nitrate fertilizer and formed a normal macro-emulsion in water.

EXAMPLE 5

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| Triclopyr acid technical (98%) | 30.0% |
| C9-11 alcohol ethoxylate | 30.0% |
| With 3 moles of EO | |
| (Contains 1% free alcohol) | |
| Tallowamine ethoxylate | 20.0% |
| Phosphate ester of an alcohol Ethoxylate | 10.0% |
| Propylene carbonate | 10.0% |

Example 5 was storage stable at ambient, 4 degrees C., and 45 degrees C. The composition mixed readily with Urea-ammonia nitrate fertilizer and formed a micro-emulsion in water.

EXAMPLE 6

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| Carfentrazone ethyl technical (90%) | 1.15% |
| C9-11 alcohol ethoxylate | 87.25% |
| With 3 moles of EO | |
| (Contains 1% free alcohol) | |
| 2,4-D acid technical (98%) | 11.6% |

Example 6 was storage stable at ambient, 4 degrees C., and 45 degrees C. The composition mixed readily with Urea-ammonia nitrate fertilizer and formed a micro-emulsion in water.

EXAMPLE 7

The following composition was prepared without adding heat on a stirrer. All liquid components were added to the beaker first, then the 2,4-D acid technical was added. Agitation was continued until the technical fully dissolved (c.a. 1 hour).

| | |
|---|---|
| Dicamba acid technical (98%) | 2.35% |
| 2,4-D acid technical (98%) | 25.90% |
| MCPP Acid technical (98%) | 6.89% |
| C9-11 alcohol ethoxylate | 33.01% |
| With 3 moles of EO | |
| (Contains 1% free alcohol) | |
| Tallowamine ethoxylate | 16.85% |
| Phosphate ester of an alcohol | 5.00% |
| Ethoxylate | |
| Water | 10.00% |

Example 7 was storage stable at ambient, 4 degrees C., and 45 degrees C. The composition mixed readily with Urea-ammonia nitrate fertilizer and formed a micro-emulsion in water.

All the references described above are incorporated by reference in its entirety for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

We claim:

1. A stabilized concentrate comprising herbicide compound in acid form and an alcohol ethoxylate surfactant, wherein the alcohol ethoxylate surfactant contains less than 2.0% free un-reacted alcohol and the alcohol ethoxylate surfactants contains, on average, less than 5 moles of ethylene oxide.

2. The concentrate of claim 1, wherein the concentrate can be combined with water to form a microemulsion.

3. The concentrate of claim 1 wherein the herbicide compound in acid form is selected from the group consisting of a phenoxy herbicide, a pyridine herbicide, a benzoic acid herbicide, a quinolinic acid herbicide, an aryloxy phenoxy propionic acid herbicide, and combinations thereof.

4. The concentrate of claim 1 wherein the herbicide acid is selected from the group consisting of 2,4-dichlorophenoxyacetic acid, dicamba acid (3,6-dichloro-O-anixic acid), 4-methyl-4-chlorophenoxyacetic acid, 2(-2-methyl-4-chlorophenoxy)propionic acid, 3,5,6-trichloro-2-pyridyloxya-cetic acid (triclopyr acid), fluazifop acid, [(4-amino-3,5-dichloro-6-fluoro-2-pyridinyl)oxy]acetic acid (fluoroxypyr acid), and combinations thereof.

5. The concentrate of claim 1 comprising herbicide compound in acid form, said alcohol ethoxylate surfactant, and essentially no organic solvent.

6. The concentrate of claim 1 comprising herbicide compound in acid form, said alcohol ethoxylate surfactant, and essentially no water.

7. The concentrate of claim 1 consisting essentially of herbicide compound in acid form and said alcohol ethoxylate surfactant.

8. The concentrate of claim 1 comprising from about 10 to about 40 parts by weight herbicide compound in acid form, and from about 60 to about 90 parts by weight said alcohol ethoxylate surfactant.

9. The concentrate of claim 1 comprising from about 20 to about 35 parts by weight herbicide compound in acid form, and from about 65 to about 80 parts by weight said alcohol ethoxylate surfactant.

10. The concentrate of claim 1 which further comprises a surfactant selected from the group consisting of an anionic surfactant, a cationic surfactant, a non-ionic surfactant, and combinations thereof.

11. The concentrate of claim 1 which further comprises a surfactant selected from the group consisting of a non-ionic linear or branched alcohol ethoxylate surfactant, an anionic phosphoric acid ester surfactant, a cationic ethoxylated tallow amine surfactant, and combinations thereof.

12. The concentrate of claim 1 further comprising a surfactant selected from the group consisting of: an ethoxylated linear alcohol; an ethoxylated amine; an ethoxylated amide; a phosphate ester; a branched alcohol ethoxylate; an ethoxylated alkyl phenol; an ethoxylated fatty acid; a sorbitan laurate; a sorbitan oleate; a propylated, ethoxylated fatty acid, alcohol, or alkyl phenol, and combinations thereof.

13. The concentrate of claim 1 consisting essentially of: from about 65 to about 80 parts by weight surfactant, from about 20 to about 35 parts by weight herbicide compound in acid form selected from the group consisting of 2,4-dichlorophenoxyacetic acid, dicamba acid (3,6-dichloro-O-anixic acid), 4-methyl-4-chlorophenoxyacetic acid, 2(-2-methyl-4-chlorophenoxy)p-ropionic acid, 3,5,6-trichloro-2-pyridyloxyacetic acid (triclopyr acid), fluazifop acid, [(4-amino-3,5-dichloro-6-fluoro-2-pyridinyl)oxy]acetic acid (fluoroxypyr acid), and combinations thereof, and no added water or added organic solvent.

14. The concentrate of claim 12 wherein the concentrate contains from about 25 to about 35 parts by weight 2,4-dichlorophenoxyacetic acid, and from about 65 to about 75 parts by weight surfactant selected from a linear alcohol ethoxylate or a combination of a linear alcohol ethoxylate and a phosphate ester.

15. A microemulsion comprising said concentrate as claimed in claim 1 and water.

16. The microemulsion of claim 15 containing no added organic solvent.

17. The microemulsion of claim 16 wherein the herbicide compound in acid form is selected from the group consisting of 2,4-dichlorophenoxyacetic acid, dicamba acid (3,6-dichloro-O-anixic acid), 4-methyl-4-chlorophenoxy- acetic acid, 2(-2-methyl-4-chlorophenoxy)propionic acid, 3,5,6-trichloro-2-pyridyloxyacetic acid (triclopyr acid), fluazifop acid, [(4-amino-3,5-dichloro-6-fluoro-2-pyridinyl)oxy]acetic acid (fluoroxypyr acid), and combinations thereof.

18. The microemulsion of claim 15 comprising: from about 0.05 to about 7 volume percent microemulsion-forming-concentrate comprising from about 10 to about 40 parts by weight herbicide compound in acid form and from about 60 to about 90 parts by weight surfactant, and from about 93 to about 99.95 volume percent water.

19. The microemulsion of claim 15 further comprising an acidifying agent.

20. The microemulsion of claim 19 wherein the acidifying agent is selected from the group consisting of phosphoric acid, carboxylic acids, or phosphate ester surfactants.

21. The microemulsion of claim 19 wherein the acidifying agent is sulfuric acid.

22. A method of applying a herbicide to a plant comprising applying the microemulsion as claimed in claim 16 to a plant to control plant growth.

23. The method of claim 22 wherein the herbicide is selected from the group consisting of 2,4-dichlorophenoxyacetic acid, dicamba acid (3,6-dichloro-O-anixic acid), 4-methyl-4-chlorophenoxyacetic acid, 2(–2-methyl-4-chlorophenoxy)propionic acid, 3,5,6-trichloro-2-pyridyloxy- cetic acid (triclopyr acid), fluazifop acid, [(4-amino-3,5-dichloro-6-fluo-ro-2-pyridinyl)oxy]acetic acid (fluoroxypyr acid), and combinations thereof.

24. The method of claim 22 further comprising adding an acidifying agent to the herbicide composition.

25. The method of claim 24 wherein the acidifying agent comprises an acid selected from the group consisting of: phosphoric acid, carboxylic acids and phosphate ester surfactants.

26. The method of claim 25 wherein the herbicide composition does not include sulfuric acid.

27. A method of applying a herbicide to a plant which comprises diluting the concentrate as claimed in claim 1 with an aqueous solution and applying it to the plant.

28. The method of claim 27 further comprising applying the herbicide composition to a plant to control plant growth, while the herbicide compound is in acid form.

29. The method of claim 27 wherein the aqueous solution is a liquid selected from the group consisting of water, a concentrated aqueous acid, and a dilute aqueous acid.

30. The concentrate as claimed in claim 1, wherein said alcohol ethoxylate surfactant is present in at least about 60 parts by weight.

* * * * *